(12) United States Patent
Kawabata

(10) Patent No.: US 7,943,231 B2
(45) Date of Patent: May 17, 2011

(54) ORGANISM SIMULATIVE PHANTOM

(75) Inventor: Ken-ichi Kawabata, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 1163 days.

(21) Appl. No.: 11/596,044

(22) PCT Filed: Dec. 13, 2004

(86) PCT No.: PCT/JP2004/018552
§ 371 (c)(1),
(2), (4) Date: Nov. 9, 2006

(87) PCT Pub. No.: WO2005/107599
PCT Pub. Date: Nov. 17, 2005

(65) Prior Publication Data
US 2008/0261009 A1  Oct. 23, 2008

(30) Foreign Application Priority Data

May 11, 2004  (JP) ................................. 2004-140811

(51) Int. Cl.
*B32B 7/02* (2006.01)
(52) U.S. Cl. .......................... 428/217; 434/267; 434/273
(58) Field of Classification Search .................. 428/217; 264/331.19; 434/267, 273
See application file for complete search history.

(56) References Cited

U.S. PATENT DOCUMENTS 4,624,143 A * 11/1986 Green .............................. 73/620
4,774,957 A * 10/1988 Nambu et al. .................. 600/414
2002/0170339 A1* 11/2002 Passi et al. ...................... 73/1.86

FOREIGN PATENT DOCUMENTS

| JP | 8-10254 A | 1/1996 |
|---|---|---|
| JP | 2002-360572 A | 12/2002 |

OTHER PUBLICATIONS

Viola F. et al., Shear Strain elastography, Proc. IEEE Ultrason Symp, Oct. 11, 2002, vol. 2, pp. 1907 to 1911.
Shizuki Ueba, et al., "Ryushi Kongo Zairyochu no Choonpa Denpan Tokusei", The Acoustical Society of Japan (ASJ), Heisei 10 Nendo Shuki Kenkyu Happyokai Koen Ronbunshu =II-, Sep. 24, 1998, pp. 1103 to 1104.
Negron L.A., et al., Development and Characterization of a Vitreous Mimicking Material for Radiation Force Imaging. IEEE Trans Ultrason Ferroelectr Freq control, 2004. 11, pp. 1543 to 1551.
International Search Report; International Application No. PCT/jP2004/018552, Jan. 25, 2005.
Yasuharu Waki, et al., "Real-time Tissue Elastography Yo Phantom no Kaihatsu", Journal of Medical Ultrasonics, Apr. 15, 2004, p. S112.
Tsuyoshi Shiina et al., "Fukugo Jiko Sokanho ni yoru Jitsujikan Tissue Elasticity Imaging", Journal of Medical Ultrasonics, Feb. 15, 1999, vol. 26, No. 2, pp. 57 to 66.
Ken-ichi Kawabata, et al., Tissue Mimicking Phantom for Ultrasonic Elastography With Finely Adjustable Elastic and Echographic Properties; 2004 IEEE Ultrasonic Symposium, p. 1502-1505.

* cited by examiner

*Primary Examiner* — Mark Ruthkosky
*Assistant Examiner* — Lawrence D Ferguson
(74) *Attorney, Agent, or Firm* — Antonelli, Terry, Stout & Kraus, LLP.

(57) ABSTRACT

Provided is a tissue mimicking phantom technology capable of controlling an ultrasonic echo intensity and hardness and offering excellent stability. A tissue mimicking phantom includes a first portion and a second portion which is incorporated in the first portion and whose hardness and/or ultrasonic echo intensity is different from that of the first portion. The first portion and second portion are gel structures that are formed with a covalent bond of macromolecular strands or a chemical bond that is as strong as the covalent bond. The gel structure has a solid scatterer (for example, metal-oxide microparticles) dispersed therein. The first portion and second portion exhibit mutually different hardness levels and ultrasonic echo intensities.

13 Claims, 7 Drawing Sheets

FIG.3
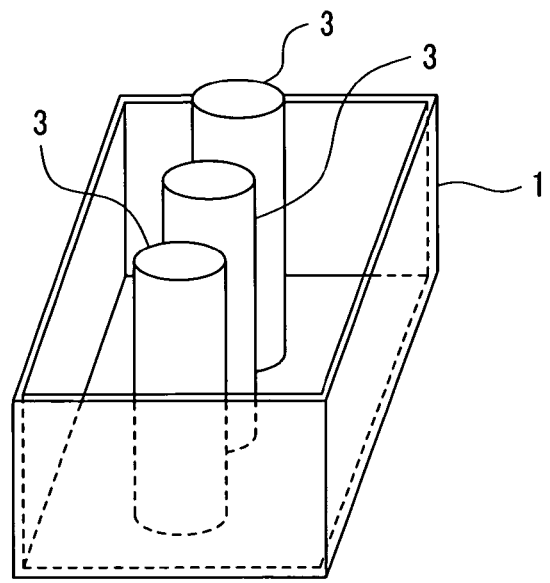
FIG.4A
FIG.4B

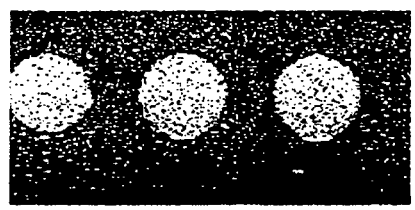
FIG.5A
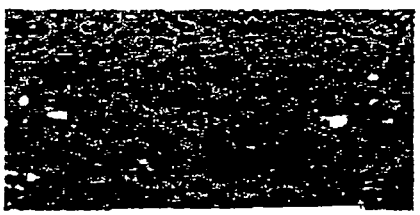
FIG.5B
FIG.6
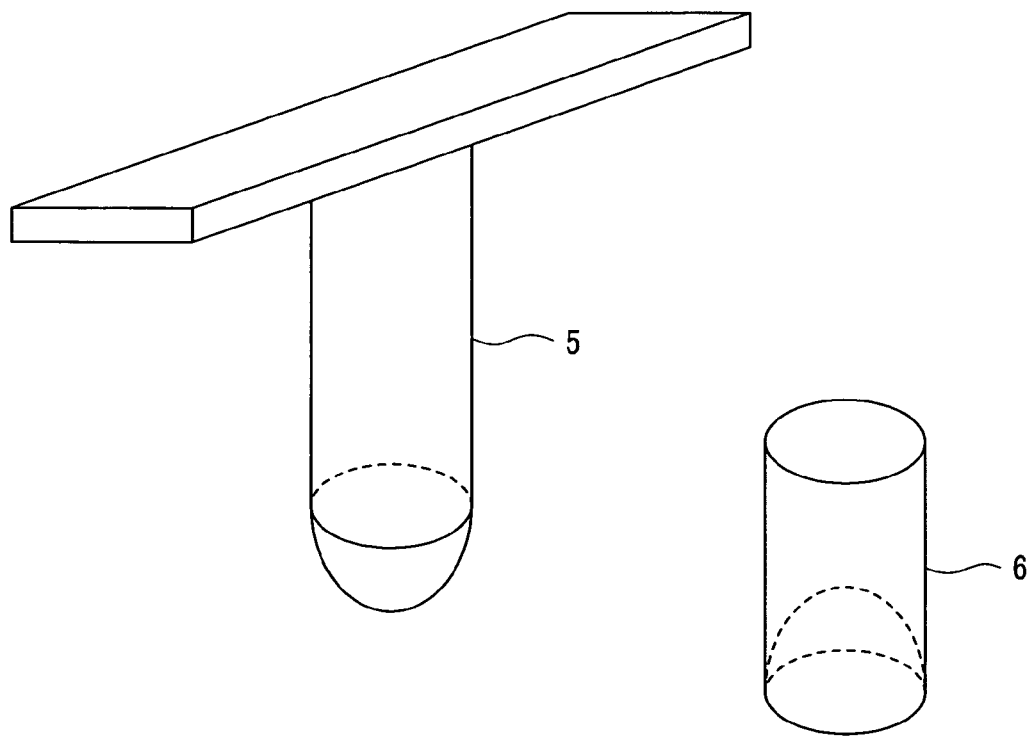

ORGANISM SIMULATIVE PHANTOM

TECHNICAL FIELD

The present invention relates to a medical diagnostic imaging technology, or more particularly, to a tissue mimicking phantom to be employed in a medical diagnostic imaging system that visualizes a lesion by utilizing differences in a modulus of shear elasticity (hardness) in a tissue.

BACKGROUND ART

Many years have passed since diagnostic imaging modalities including X-ray computed tomography (CT), magnetic resonance imaging (MRI), and diagnostic ultrasound became indispensable in medical practices. The modalities are designed to image differences in a CT value in a tissue, differences in a nuclear spin relaxation time, or differences in acoustic impedance. Since the differences in a physical nature reflect the structure (shape) of a tissue, the imaging is referred to as morphological imaging. In contrast, imaging of a region in a tissue that is structurally identical to the other region therein but is functionally different therefrom is referred to as functional imaging.

In recent years, visualization of the state of the brain or a tumorous region through positron emission tomography (PET) has especially attracted attention. The PET is a technique of handling radioactively metabolized molecules so as to perform functional imaging on the level of molecules. In contrast, as functional imaging to be performed on the level of tissues, there is elasticity imaging that is a technique of imaging differences in hardness in a tissue. This technique is intended to acquire information, which is supposed to be acquired through physician's palpation, using a diagnostic system. As a lump leads to early diagnosis of breast cancer, so hardness becomes a significant factor that reflects a cancerous tissue or the like. Supposing the hardness of a microscopic region can be imaged using a diagnostic system, arteriosclerosis can be examined or a pathology that cannot be revealed by palpation can be diagnosed.

Hardness to be examined by palpation is represented by a modulus of rigidity (a modulus of shear elasticity). For imaging of moduli of elasticity, a technique is often adopted that: an operator presses a probe against a body surface; and a local deformation (distortion) factor of an intracorporeal tissue is calculated in order to detect a hardness distribution. The modulus of shear elasticity is one of physical quantities that are hard to accurately measure. Moreover, elasticity imaging proves its worth in imaging of an early-phase lesion that is hard to distinguish through normal diagnostic imaging. Therefore, relative moduli of elasticity other than absolute moduli of elasticity are calculated in order to visualize a lesion. The diagnosis based on the relative moduli of elasticity has become a mainstream in clinical practices.

The elasticity imaging provides an unprecedented diagnostic technique. For prevalence of the technique, in addition to training of an operator and demonstration or discussion of the technique, a tissue mimicking phantom is needed.

A conventionally known phantom for elasticity imaging is based on an existing phantom designed for normal ultrasonic echography. The fundamental structure of the phantom is such that graphite or any other powder is mixed in a gel of a polymer such as agar or gelatin. The gel has solvent molecules bound in a macromolecular network, and is apparently solid. A hydro-gel prepared by adopting water as a solvent has the same acoustic property as water and a soft tissue of a tissue. Acoustically, the hydro-gel can substantially be regarded as a simulation of a tissue. Since the hardness of the gel can be readily controlled by changing a macromolecular concentration or any other condition for production, the hydro-gel is an excellent material for an elasticity imaging phantom.

In general, a macromolecular strand included in a hydro-gel and water are hardly different from each other in terms of acoustic impedance. The use of a gel alone cannot sufficiently produce ultrasonic echoes. Therefore, as mentioned above, a powder such as graphite whose acoustic impedance is different from the acoustic impedance of water is mixed in the gel. Ultrasonic echoes to be returned from the entire gel can be controlled by adjusting ultrasonic echoes to be returned from the interface between the powder and water. Based on this idea, a phantom is produced as mentioned in, for example, "1996 IEEE Ultrasonic Symposium" (p. 1502-1505).

Moreover, a gel of agar or gelatin is referred to as a thermally-reversible gel, and reversibly changes between a sol (highly fluid state) and the gel (less fluid state). The gel whose states change with temperature has macromolecular networks thereof bonded relatively loosely and is therefore mechanically less strong.

As a solution, a method using a polyvinyl alcohol gel that exhibits low thermal reversibility despite its preparation including steps of heating and cooling has been proposed as described in Japanese Patent Application Laid-Open No. 8-10254.

DISCLOSURE OF THE INVENTION

Problems to be Solved by the Invention

In preparation of a thermally-reversible gel, introduction of a scatterer into a gel is performed in a state of a sol, that is, in a high-temperature state. Thereafter, cooling should be performed for gelling. The sol-to-gel transition takes places in the range from approximately 30 to 50° C. in the case of agar or from approximately 20 to 40° C. in the case of gelatin. When the scatterer is introduced into the sol, the scatterer should be held at a temperature that is about 70° C. or much higher than the temperature for gelling. At the high temperature of about 70° C., a vapor pressure of water is so high that evaporation progresses. This makes it hard to accurately control a concentration. Moreover, especially when a hard gel is prepared, a high-concentration polymer should be adopted. Therefore, the sol is highly viscous, and it is hard to homogeneously mix powder in a highly viscous solution. Consequently, when a thermally-reversible gel is adopted, there is difficulty in achieving dispersion of a scatterer in a highly reproducible and highly homogeneous manner. This poses a problem in that an ultrasonic echo intensity becomes hard to control.

In order to cope with low mechanical strength, a method using a polyvinyl alcohol gel like the one disclosed in the related art (Non-patent Document 1) has been proposed. In the case of an ordinary thermally reversible gel of agar or gelatin, a change in a three-dimensional polymeric structure derived from a drop in temperature from the temperature for a sol brings about interaction of macromolecules. This results in formation of a gel network. In contrast, in the case of the polyvinyl alcohol gel, the drop in temperature from the temperature for the sol freezes free water in a solution. Consequently, when water separates from a macromolecular strand, polyvinyl alcohol molecules approach one another and hydrogen bonding occurs among the molecules. This results in formation of a gel network. Therefore, repetition of heating and freezing causes the gel network to grow and eventually provides a robust gel structure. Owing to the principle, when the polyvinyl alcohol gel is adopted as a raw material, a phantom that is more mechanically robust than a phantom made from the thermally reversible gel of agar or gelatin can be produced.

However, the difficulty in homogeneously dispersing a scatterer is not overcome with the adoption of a polyvinyl alcohol gel. Besides, the polyvinyl alcohol gel has a network formed through weaker bonding than hydrogen bonding that is covalent bonding. Although the polyvinyl alcohol gel exhibits higher mechanical strength than a fully thermally reversible gel, it changes time-sequentially. Incidentally, the gel of agar, gelatin, or polyvinyl alcohol has a network formed through weaker chemical bonding such as intermolecular reaction or hydrogen bonding. This kind of gel is referred to as a physical gel. In contrast, a gel having a network formed through strong bonding such as covalent bonding is referred to as a chemical gel.

As mentioned above, known elasticity imaging phantoms are made from the physical gel. Therefore, dispersion of a scatterer is inhomogeneous and less reproducible. Moreover, mechanical strength is low, and time-sequential stability is poor.

The present invention addresses the foregoing problems. An object of the present invention is to provide a tissue mimicking phantom technology capable of controlling an ultrasonic echo intensity and hardness and offering excellent stability.

Means for Solving the Problems

In order to accomplish the above object, the present inventor et al. have found the usefulness of a chemical gel that is prepared according to a method in which: a network structure is formed with a covalent bond of macromolecular strands or a chemical bond that is as strong as the covalent bond; and a step of producing the macromolecules through polymerization of monomers and a step of forming the network by bonding macromolecular strands proceed concurrently.

When macromolecules bond through covalent bonding, the low stability that is a bottleneck hindering adoption of a physical gel is overcome. Furthermore, when the polymerization step and the network formation step proceed concurrently, a scatterer can be dispersed in a monomeric (low molecular) solution exhibiting low viscosity. Consequently, the scatterer can be homogeneously dispersed in the gel with high reproducibility. Furthermore, since the preparation of the chemical gel does not, unlike the preparation of the physical gel, include steps of heating and cooling, the concentration of the scatterer can be strictly set to a specific value.

A chemical gel employed in the present invention should have a network formed concurrently with monomeric polymerization. An example of the gel is a gel containing a polyacrylamide derivative expressed by chemical formula (1) presented below (where $R_1$ and $R_2$ may denote the same chemical structure or different chemical structures in which an alkyl group composed of twenty or less hydrogen atoms and carbon atoms or an alkyl group composed of twenty or less carbon atoms includes at least one of a hydroxyl group, a sulfone group, an ether bond, and nitrogen atoms).

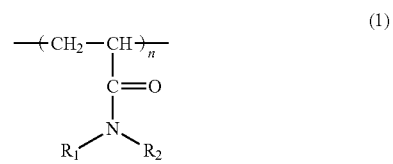

As for a polymerization method, no restrictions are especially imposed. Either a reaction of addition polymerization in the presence of a divinyl compound or a reaction of concentration polymerization of a multifunctional compound may be adopted. Reactions of polymerization that may be employed in preparation of a gel in the present invention include, for example, polycondensation, thermal polymerization, radiation-induced polymerization, photo-polymerization, and plasma polymerization. A method especially preferable from the viewpoint of easy handling is of adding a polymerization initiator (in some cases, a polymerization accelerator) to a mixed solution of a monomer that is a major component of a macromolecular strand including two or more functional groups and a cross-linking monomer including three or more functional groups. The cross-linking monomer is determined depending on the monomer to be adopted as the major component of the macromolecular strand. When the monomer of the polyacrylamide derivative is employed, N,N'-methylenebis (acrylamide) is suitable.

Moreover, for accomplishment of the aforesaid object, it would prove effective to adopt as a scatterer microparticles having a smaller diameter instead of powder such as graphite. This is because there is difficulty in initiating gelling instantaneously. In the case of particles whose diameter exceeds 10 μm such as graphite powder employed in ultrasonic echography phantoms, sedimentation occurring in the course of gelling cannot be ignored. As for a physical gel, since powder is mixed in a highly viscous polymeric solution, the sedimentation can be prevented to some extent. However, for a chemical gel, a scatterer is mixed in a less viscous monomeric solution for the purpose of gelling. How to prevent the sedimentation has therefore a significant meaning. Supposing spherical particles are monodisperse, a sedimentation velocity of the particles in a fluid is provided by the Stokes equation presented below:

$$V = g(\rho s - \rho O)d^2/18\eta$$

where V denotes a sedimentation velocity, g denotes a gravitational acceleration, ρs denotes a particulate density, ρO denotes the density of a solvent, d denotes a particulate diameter, and η denotes a coefficient of viscosity. For example, assuming that the diameter of particles is 40 μm and the specific gravity thereof is 4, the sedimentation velocity of the particles in water is 1.6 μm/s. Assuming that gelling requires ten min., the particles sediment about 6 cm during the gelling. In contrast, when the diameter of particles is 4 μm, the sedimentation velocity thereof is 16 nm/s, and a sedimentation distance to be attained for ten min. is as negligible as approximately 0.6 mm. The gelling time varies depending on the shape or size of a phantom. An optimal size of a scatterer varies depending on an intended phantom. The specific gravities of metals, metallic oxides, carbon particles, or spherical polymers that can be adopted as the scatterer in the form of solid particles generally range from 1 to 5. Therefore, when microparticles whose diameter is equal to or smaller than 5 μm are adopted, as long as the sedimentation distance to be attained for one min. that is considered as the shortest gelling time is about 1 mm, the scatterer can be homogeneously dispersed. The raw material of the scatterer employed in the present invention is not limited to any specific one as long as the material is a little water-soluble solid. For the viewpoint of mechanical stability, oxidic microparticles of titanium oxide, aluminum oxide, or silicone oxide, metallic microparticles of tungsten, nickel, or molybdenum, and resin particles such as polyethylene particles, polyethylene hollow spheres, or polystyrene hollow spheres are preferred as the scatterer.

Typical examples of the constitution of the present invention will be described below.

(1) A tissue mimicking phantom in accordance with the present invention is a tissue mimicking phantom whose multiple portions are different from one another in terms of hardness and an ultrasonic echo property. The multiple portions contain a gel structure having a liquid bound in a polymeric framework, and also contain a solid scatterer.

(2) In the tissue mimicking phantom set forth in item (1), the multiple portions contain an irreversible gel cross-linked through chemical bonding.

(3) In the tissue mimicking phantom set forth in item (2), the gel structure contains a polyacrylamide derivative expressed by the chemical formula presented below:

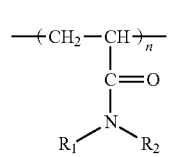

(2)

where $R_1$ and $R_2$ denote a chemical structure in which an alkyl group composed of twenty or less hydrogen atoms and carbon atoms or an alkyl group composed of twenty or less carbon atoms contains at least one of a hydroxyl group, a sulfone group, an ether bond, and nitrogen atoms.

(4) In the tissue mimicking phantom set forth in item (1), the solid scatterer contains at least one kind of oxidic microparticles.

(5) In the tissue mimicking phantom set forth in item (4), the oxidic microparticles include at least one of titanium-oxide microparticles, aluminum-oxide microparticles, and silicone-oxide microparticles.

(6) In the tissue mimicking phantom set forth in item (1), the solid scatterer contains at least one kind of metallic particles.

(7) In the tissue mimicking phantom set forth in item (1), the solid scatterer contains at least one kind of resin particles.

(8) In the tissue mimicking phantom set forth in item (7), the resin particles include at least one of polyethylene particles, polyethylene hollow spheres, and polystyrene hollow spheres.

(9) An tissue mimicking phantom in accordance with the present invention includes a first portion, and a second portion which is incorporated in the first portion and whose hardness and/or ultrasonic echo intensity is different from that of the first portion does. The first portion and second portion are gel structures formed with a covalent bond of macromolecular strands or a chemical bond that is as strong as the covalent bond. The gel structure has a solid scatterer dispersed therein. The first and second portions exhibit mutually different hardness levels and ultrasonic echo intensities.

(10) A tissue mimicking phantom manufacturing method in accordance with the present invention is a method of manufacturing a tissue mimicking phantom that includes a first portion and a second portion which is incorporated in the first portion and whose hardness and ultrasonic echo property are different from those of the first portion. The manufacturing method includes: a step of gelling a solution, which contains a polyacrylamide derivative expressed by the chemical formula presented below and metal-oxide microparticles, in a female mold which contours the first portion and in which a male mold contouring the second portion is incorporated; a step of removing the male mold from the first portion formed in the female mold; a step of pouring a dispersing agent, which contains the polyacrylamide derivative expressed by the chemical formula presented below and the metal-oxide microparticles, into a hold in the female mold created by removing the male mold, and gelling the dispersing agent so as to form the second portion; and a step of taking out a gel composed of the first portion and second portion from the female mold:

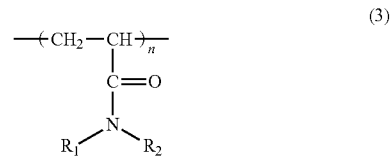

(3)

where $R_1$ and $R_2$ denote a chemical structure in which an alkyl group composed of twenty or less hydrogen atoms and carbon atoms or an alkyl group composed of twenty or less carbon atoms contains at least one of a hydroxyl group, a sulfone group, an ether bond, and nitrogen atoms.

EFFECT OF THE INVENTION

According to the present invention, there is provided a tissue mimicking phantom technology capable of controlling an ultrasonic echo intensity and hardness and offering excellent stability.

BRIEF DESCRIPTION OF THE DRAWINGS

FIG. 3 shows an example of a combination of the female mold and male molds for use in manufacturing the tissue phantom in accordance with the first embodiment of the present invention;

FIG. 4A and FIG. 4B show examples of an ultrasonic echographic image and an elasticity imaging image respectively of the tissue mimicking phantom in accordance with the first embodiment of the present invention;

FIG. 5A and FIG. 5B show examples of an ultrasonic echographic image and an elasticity imaging image respectively of a tissue mimicking phantom in accordance with the second embodiment of the present invention;

FIG. 6 shows an example of an auxiliary male mold for use in manufacturing a tissue mimicking phantom in accordance with the third embodiment of the present invention;

BEST MODE FOR CARRYING OUT THE INVENTION

Figure 1:
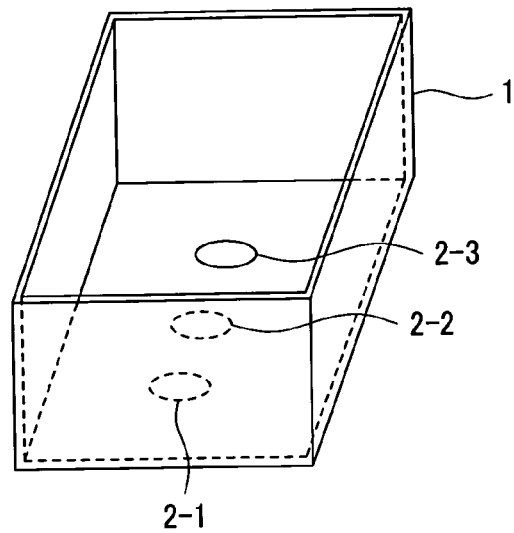
FIG. 1 shows an example of a female mold for use in manufacturing a tissue mimicking phantom in accordance with the first embodiment of the present invention.

Referring to the drawings, embodiments of the present invention will be described below.

First Embodiment

As the first embodiment of the present invention, a phantom for two-dimensional display of a distribution of moduli of elasticity that has multiple internal regions which are hard and different from each other in terms of an ultrasonic-image brightness will be described below.

Figure 2:
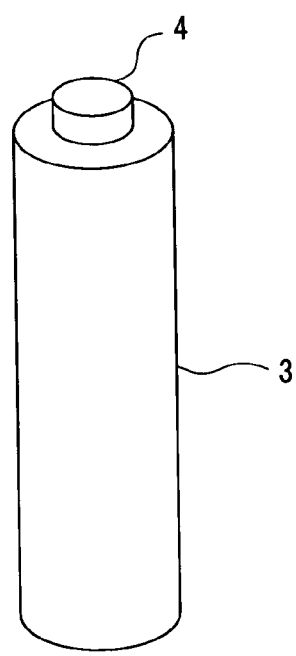
FIG. 2 shows an example of a male mold for use in manufacturing the tissue phantom in accordance with the first embodiment of the present invention.

For manufacturing of a two-dimensional display phantom, a female mold 1 having, as shown in FIG. 1, a size and a shape (herein, a rectangular parallelepiped) desired for a phantom is procured. Moreover, male molds 3 that are, as shown in FIG. 2, shaped by axially elongating a desired planar shape (herein a circle) and that are equivalent to portions of the phantom exhibiting a different acoustic property or elasticity. In FIG. 1, reference numerals 2-1, 2-2, and 2-3 denote recesses in the female mold 1 in which the male molds 3 are locked. Lock portions 4 of the respective male molds 3 are fitted into the recesses 2-1, 2-2, and 2-3 respectively. Depending on the shape of the male molds 3, the ends of the male molds 3 may be screwed into the respective recesses 2.

Thereafter, as shown in FIG. 3, the male molds 3 are secured in the female mold 1 (herein, three male molds 3 are employed). A 500 ml solution is prepared by mixing 80 ml of a 40%-diluted acrylamide solution (out of 1000 ml of a stock prepared by mixing 390 g of acrylamide and 10 g of N,N'-methylenebisacrylamide in distilled water) and 12.5 g of titanium-oxide microparticles (for example, P-25 manufactured by Nippon Aerosil Co., Ltd.) in distilled water. The solution is deaerated while being stirred for 30 min. Thereafter, 5 ml of a 10%-diluted ammonium persulfite (APS) solution and 0.2 ml of N,N,N',N'-tetramethylethylenediamine (TEMED) solution are added to the solution. The resultant solution is immediately poured into the female mold 1 for fear it may foam up, and the female mold is then covered for the purpose of gelling. At this time, the entire container is held at an ice point in order to prevent a rise in temperature to be caused by heat dissipation derived from polymerization. After the gelling is confirmed, the male molds 3 are removed motionlessly.

Thereafter, (A) a 25 ml dispersing agent prepared by mixing 9 ml of an acrylamide solution and 1 g of titanium-oxide microparticles in distilled water, (B) a 25 ml dispersing agent prepared by mixing 9 ml of the acrylamide solution and 0.6 g of the titanium-oxide microparticles in distilled water, and (C) a 25 ml dispersing agent prepared by mixing 9 ml of the acrylamide solution and 0.01 g of the titanium-oxide microparticles are deaerated while being stirred for five min. Thereafter, 0.25 ml of an APS solution and 0.01 ml of a TEMED solution are added to each of the dispersing agents. The resultant dispersing agents (A), (B), and (C) are poured into the respective holes created by removing the male molds 3. The female mold is covered for the purpose of gelling. After the gelling is completed, a gel is taken out of the female mold 1. Thus, the two-dimensional display phantom is manufactured.

FIG. 4A and FIG. 4B show examples of an ultrasonic echographic image and an elasticity imaging image respectively of the tissue mimicking phantom in accordance with the present invention which is produced by preparing materials so that the internal portions will exhibit the same ultrasonic echo intensity as the surrounding portion will but exhibit different hardness levels. In the ultrasonic echographic image, the portion exhibiting a higher ultrasonic echo intensity is visualized more whitely. Moreover, in the elasticity imaging image, a harder portion is visualized more whitely. Three circular areas appear in the ultrasonic echographic image with different brightness levels, while they appear in the elasticity imaging image so as to express nearly the same hardness that is higher than the hardness expressed by the surrounding area. The results demonstrate that the phantom makes it possible to control the hardness and ultrasonic echo intensity.

As for the shape of the male molds, not only a circle but also a polygon such as a triangle or a square and an ellipse will do. Moreover, acrylamide may be replaced with any of methacrylic acid 2-(dimethylamino)ethyl, 2-dimethylaminoethyl-methacrylate, 2-acrylamido-2-methylpropanesulfonic acid, N-acryloylaminoethoxyethanol, N-acryloylaminopropanol, and N-methylolacrylamido. Nevertheless, a similar phantom can be produced. Moreover, titanium oxide may be replaced with any of silicone oxide, aluminum oxide, graphite, polystyrene, and polyethylene. Nevertheless, a similar phantom can be produced.

Second Embodiment

As the second embodiment of the present invention, a phantom for two-dimensional display of a distribution of moduli of elasticity which has multiple internal regions whose hardness is identical to the hardness of the surrounding region and whose ultrasonic-image brightness levels are different from one another will be described below.

A female mold 1 and male molds 3 identical to those employed in the first embodiment are adopted. As shown in FIG. 3, the male molds 3 are secured in the female mold 1 (herein, three male modes 3 are employed). A solution of 500 ml is prepared by mixing 80 ml of a 40%-diluted acrylamide solution (out of 1000 ml of a stock prepared by mixing 390 g of acrylamide and 10 g of N,N'-methylenebisacrylamide in distilled water) and 12.5 g of titanium-oxide microparticles (for example, P-25 manufactured by Nippon Aerosil Co., Ltd.) in distilled water. The solution is deaerated while being stirred for thirty min. Thereafter, 5 ml of a 10%-diluted ammonium persulfite (APS) solution and 0.2 ml of a N,N,N', N'-tetramethylethylenediamine (TEMED) solution are added to the solution. The resultant solution is poured into the female mold 1 motionlessly for fear it may foam up. The female mold is then covered for the purpose of gelling. At this time, the entire container is held at an ice point in order to prevent a rise in temperature to be caused by heat dissipation derived from polymerization. After the gelling is confirmed, the male molds 3 are motionlessly removed.

Thereafter, (A) 25 ml of a dispersing agent prepared by mixing 3 ml of an acrylamide solution and 1 g of titanium-oxide microparticles in distilled water, (B) 25 ml of a dispersing agent prepared by mixing 3 ml of the acrylamide solution and 0.6 g of the titanium-oxide microparticles in distilled water, and (C) 25 ml of a dispersing agent prepared by mixing 3 ml of the acrylamide solution and 0.01 g of the titanium-oxide microparticles in distilled water are deaerated while being stirred for five min. Thereafter, 0.25 ml of an APS solution and 0.01 ml of a TEMED solution are added to each of the dispersing agents. The resultant dispersing agents (A), (B), and (C) are poured into respective holes created by removing the male molds 3. The female mold is then covered for the purpose of gelling. After the gelling is completed, a gel is taken out of the female mold 1. Thus, a two-dimensional display phantom is manufactured.

FIG. 5A and FIG. 5B show examples of an ultrasonic echographic image and an elasticity imaging image respectively of the tissue phantom in accordance with the present invention. In the ultrasonic echographic image, a portion exhibiting a higher ultrasonic echo intensity is visualized more whitely. In the elasticity imaging image, a harder portion is visualized more whitely. In the ultrasonic echographic image, three circular areas appear with different brightness levels. In the elasticity imaging image, the three circular areas appear to indicate the same hardness. The results demonstrate that the phantom makes it possible to control the hardness and ultrasonic echo intensity.

As for the shape of the male molds, not only a circle but also a polygon such as a triangle or a square or an ellipse may be adopted. Moreover, acrylamide may be replaced with any of methacrylic acid 2-(dimethylamino)ethyl, 2-dimethylaminoethylmethacrylate, 2-acrylamide-2-methylpropanesulfonic acid, N-acryloylaminoethoxyethanol, N-acryloylaminopropanol, and N-methylolacrylamide. Nevertheless, a similar phantom can be produced. Moreover, titanium oxide may be replaced with any of silicone oxide, aluminum oxide, graphite, polystyrene, and polyethylene. Nevertheless, a similar phantom can be produced.

Third Embodiment

As a third embodiment of the present invention, a phantom for three-dimensional display of a distribution of moduli of elasticity will be described below.

For production of a three-dimensional display phantom, similarly to that of the two-dimensional display phantom, a female mold 1 having, as shown in FIG. 1, a size and a shape desired for a phantom (herein a rectangular parallelepiped) is procured. Moreover, male molds 5 and auxiliary male molds 6 each pair of which is, as shown in FIG. 6, used to create a desired three-dimensional shape (herein a sphere) equivalent to a portion of the phantom exhibiting a different acoustic property or elasticity.

Figure 7:
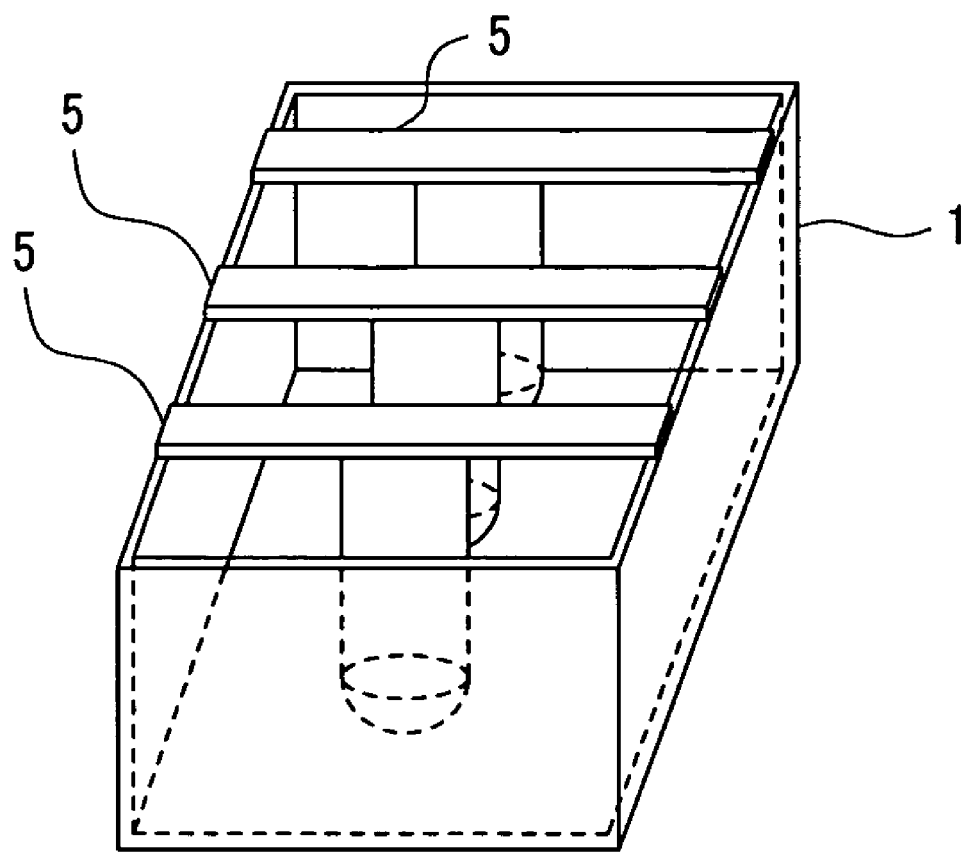
FIG. 7 shows an example of a combination of the female mold and auxiliary male molds for use in manufacturing the tissue mimicking phantom in accordance with the third embodiment of the present invention.

Thereafter, the male molds 5 are, as shown in FIG. 7, secured in the female mold 1. A 500 ml solution is prepared by mixing 80 ml of a 40%-diluted acrylamide solution (out of 1000 ml of a stock prepared by mixing 390 g of acrylamide and 10 g of N,N'-methylenebisacrylamide in distilled water) and 12.5 g of titanium-oxide microparticles (P-25 manufactured by Nippon Aerosil Co., Ltd.) in distilled water. The solution is deaerated while being stirred for thirty min. Thereafter, 5 ml of a 10%-diluted ammonium persulfite (APS) solution and 0.2 ml of a N,N,N',N'-tetramethylethylenediamine (TEMED) solution are added to the solution. The resultant solution is poured into the female mold 1 for fear it may foam up. The female mold is then covered for the purpose of gelling. At this time, supposing heat is dissipated due to polymerization, the female mold 1 may be cooled in advance. After the gelling is confirmed, the male molds 5 are motionlessly removed.

Thereafter, (A) a 25 ml dispersing agent prepared by mixing 3 ml of an acrylamide-solution and 1 g of titanium-oxide microparticles in distilled water, (B) a 25 ml dispersing agent prepared by mixing 3 ml of the acrylamide solution and 0.6 g of the titanium-oxide microparticles in distilled water, and (C) a 25 ml dispersing agent prepared by mixing 3 ml of the acrylamide solution and 0.01 g of the titanium-oxide microparticles in distilled water are deaerated while being stirred for five min. Thereafter, 0.25 ml of an APS solution and 0.01 ml of a TEMED solution are added to each of the dispersing agents. The resultant dispersing agents are poured into respective holes created by removing the male molds 5. The holes are then covered by the auxiliary male molds 6 respectively for the purpose of gelling. After the gelling is completed, the auxiliary male molds 6 are removed. Then, a 25 ml dispersing agent prepared by mixing 4 ml of the acrylamide solution and 12.5 g of the titanium-oxide microparticles in distilled water is deaerated while being stirred for five min. Thereafter, 0.25 ml of the APS solution and 0.01 ml of the TEMED solution are added to the dispersing agent, and the female mold having the auxiliary molds removed is covered for gelling. After the gelling is completed, a gel is taken out of the female mold 1. Thus, a three-dimensional display phantom is manufactured.

Owing to the combination of the male mold 5 and auxiliary male mold 6, not only a sphere but also a pyramidal or conical body such as a trigonal pyramid, a quadrangular pyramid, or a cone or a rotary elliptic body may be adopted as a portion of a phantom exhibiting a different acoustic property or elasticity. Moreover, acrylamide may be replaced with any of methacrylic acid 2-(dimethylamino)ethyl, 2-dimethylaminoethylmethacrylate, 2-acrylamide-2-methylpropanesulfonic acid, N-acryloylaminoethoxyethanol, N-acryloylaminopropanol, and N-methylolacrylamide. Nevertheless, a similar phantom can be produced. Moreover, titanium oxide may be replaced with any of silicone oxide, aluminum oxide, graphite, polystyrene, and polyethylene. Nevertheless, a similar phantom can be produced.

Fourth Embodiment

As the fourth embodiment of the present invention, a phantom for two-dimensional display of a distribution of moduli of elasticity that includes an internal region which is harder than the surrounding region and whose ultrasonic-image brightness is identical to that of the surrounding region will be described below.

Figure 8:
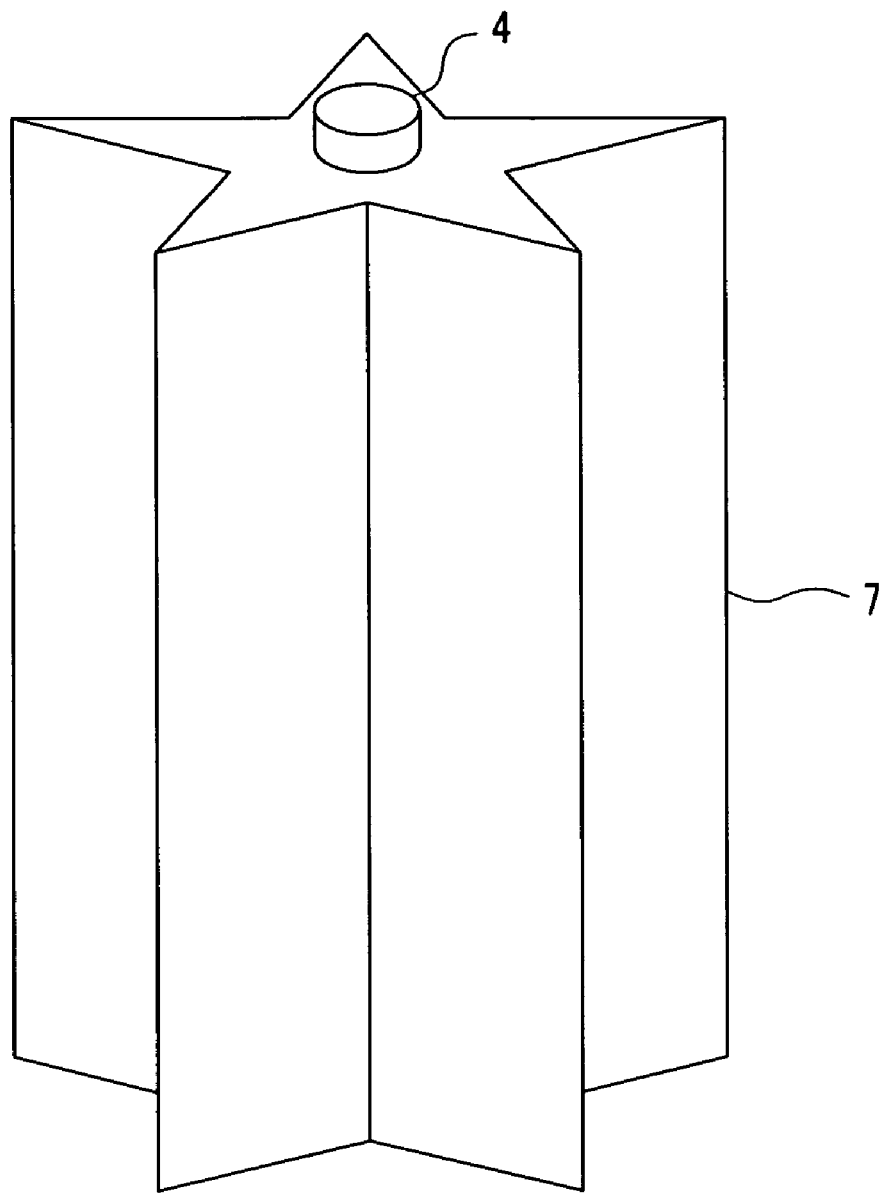
FIG. 8 shows an example of a male mold for use in manufacturing a tissue mimicking phantom in accordance with the fourth embodiment of the present invention.
Figure 9:
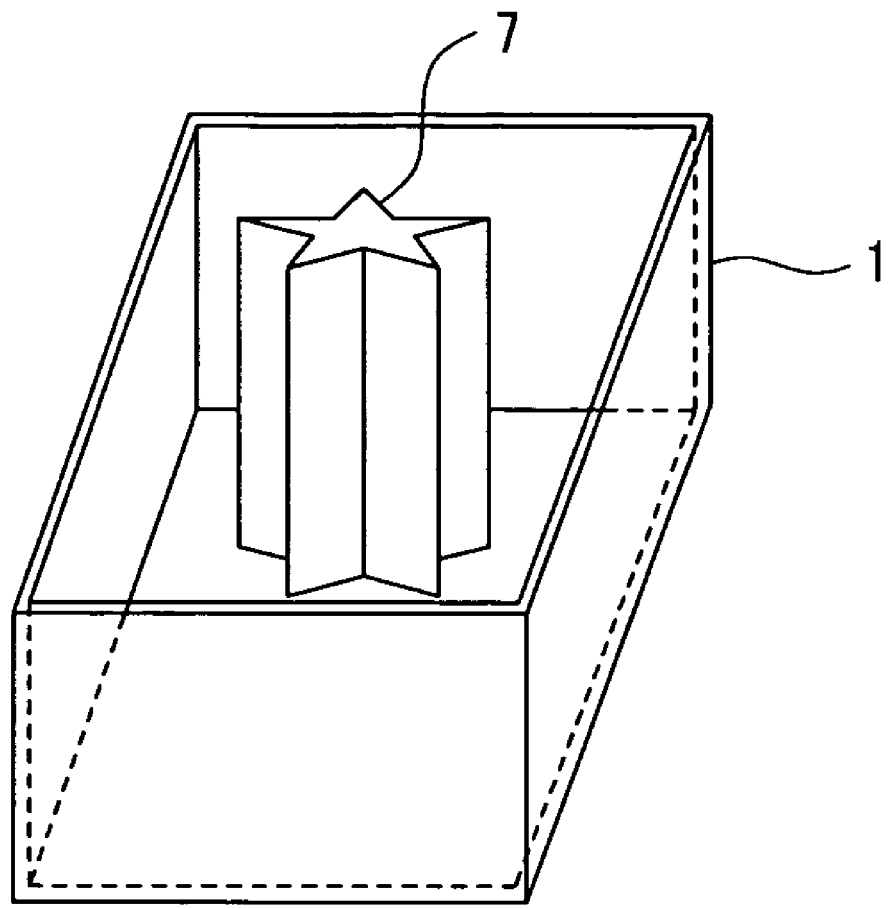
FIG. 9 shows an example of a combination of the female mold and male mold for use in manufacturing the tissue mimicking phantom in accordance with the fourth embodiment of the present invention.

A female mold 1 identical to that employed in the first embodiment and a male mold 7 shown in FIG. 8 are employed. As shown in FIG. 9, the male mold 7 is secured in the female mold 1. A 500 ml solution is prepared by mixing 80 ml of a 40%-diluted acrylamide solution (out of 1000 ml of a stock prepared by mixing 390 g of acrylamide and 10 g of N,N'-methylenebisacrylamide in distilled water) and 12.5 g of silicone-oxide microparticles (Aerosil200 manufactured by Nippon Aerosil Co., Ltd.) in distilled water. The solution is deaerated while being stirred for thirty min. Thereafter, 5 ml of a 10%-diluted ammonium persulfite (APS) solution and 0.2 ml of a N,N,N',N'-tetramethylethylenediamine (TEMED) solution are added to the solution. The resultant solution is poured into the female mold 1 for fear it may foam up, and the female mold is covered for the purpose of gelling. At this time, the entire container is held at an ice point in order to prevent a rise in temperature caused by heat dissipation stemming from polymerization. After the gelling is confirmed, the male mold 7 is motionlessly removed. Thereafter, a 25 ml dispersing agent prepared by mixing 3 ml of the acrylamide solution and 0.6 g of the silicon-oxide microparticles in distilled water is deaerated while being stirred for five min. Then, 0.25 ml of the APS solution and 0.01 ml of the TEMED solution are added to the dispersing agent. The resultant dispersing agent is poured into a hole created by removing the male mold 7. The female mold is then covered for gelling. After the gelling is completed, a gel is taken out of the female mold 1. Thus, a two-dimensional display phantom is manufactured.

Figure 10A:
FIG. 10A and FIG. 10B show examples of an ultrasonic echographic image and an elasticity imaging image respectively of the tissue mimicking phantom in accordance with the fourth embodiment of the present invention.
Figure 10B:
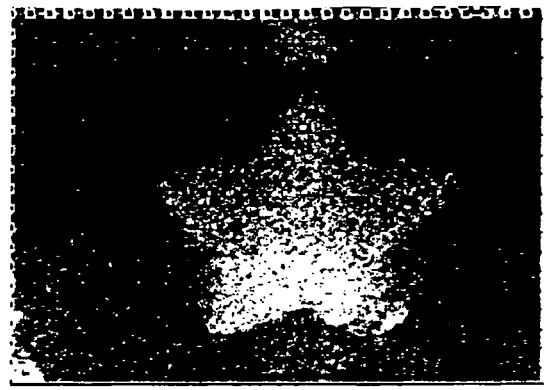

FIG. 10A and FIG. 10B show an ultrasonic echographic image and an elasticity imaging image respectively of the produced gel. In the ultrasonic echographic image, a portion exhibiting a higher ultrasonic echo intensity is visualized more whitely. In the elasticity imaging image, a harder portion is visualized more whitely. In the ultrasonic echographic image, the brightness is nearly even throughout the image. In the elasticity image, a star-shaped area appears to indicate a higher hardness level. The results demonstrate that the phantom makes it possible to control the hardness and ultrasonic echo Moreover, acrylamide may be replaced with any of methacrylic acid 2-(dimethylamino)ethyl, 2-dimethylaminoethylmethacrylate, 2-acrylamide-2-methylpropanesulfonic acid, N-acrylolaminoethoxyethanol, N-acrylolaminopropanol, and N-methylolacrylamide. Nevertheless, a similar phantom can be produced. Moreover, silicone oxide may be replaced with any of titanium oxide, aluminum oxide, graphite, polystyrene, and polyethylene. Nevertheless, a similar phantom can be produced.

INDUSTRIAL APPLICABILITY

As described so far, a tissue mimicking phantom in accordance with the present invention makes it possible to control an ultrasonic echo intensity and hardness, and can be used to evaluate an elasticity imaging system, to train an operator, or to demonstrate elasticity imaging.

DESCRIPTION OF REFERENCE NUMERALS

1 . . . Female mold for use in manufacturing a phantom
2 . . . Recess for use in manufacturing a phantom
3 . . . Male mold for use in manufacturing a phantom
4 . . . Lock portion for to be fitted to a female mold
5 . . . Male mold for use in manufacturing a phantom
6 . . . Auxiliary male mold for use in manufacturing a phantom
7 . . . Star-shaped male mold for use in manufacturing a phantom

The invention claimed is:

1. A tissue mimicking phantom including a plurality of portions that is different from one another in terms of hardness and an ultrasonic echo property, wherein:
the plurality of portions contains a gel structure having a liquid bound in a polymeric framework, and also contains a solid scatterer, and wherein the plurality of portions contains an irreversible gel cross-linked through chemical bonding.

2. The tissue mimicking phantom according to claim 1, wherein the gel structure contains a polyacrylamide derivative expressed by a chemical formula presented below:

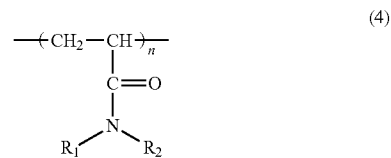

wherein $R_1$ and $R_2$ each denote a chemical structure in which an alkyl group composed of twenty or less hydrogen atoms and carbon atoms or an alkyl group composed of twenty or less carbon atoms contains at least one of a hydroxyl group, a sulfone grope, an ether bond, and nitrogen atoms.

3. The tissue mimicking phantom according to claim 1, wherein the solid scatterer contains at least one kind of oxidic microparticles.

4. The tissue mimicking phantom according to claim 1, wherein the solid scatterer contains at least one kind of oxidic microparticles, and wherein the oxidic microparticles include at least one of titanium-oxide microparticles, aluminum-oxide microparticles, and silicon-oxide microparticles.

5. The tissue mimicking phantom according to claim 1, wherein the solid scatterer contains at least one kind of metallic particles.

6. The tissue mimicking phantom according to claim 1, wherein the solid scatterer contains at least one kind of resin particles.

7. The tissue mimicking phantom according to claim 1, wherein the solid scatterer contains at least one kind of resin particles, and wherein the resin particles include at least one of polyethylene particles, polyethylene hollow spheres, and polystyrene hollow spheres.

8. A tissue mimicking phantom including a plurality of portions that is different from one another in terms of hardness and an ultrasonic echo property, wherein:
the plurality of portions contains a gel structure having a liquid bound in a polymeric framework, and also contains a solid scatterer, and
wherein the solid scatterer contains at least one kind of oxidic microparticles.

9. The tissue mimicking phantom according to claim 8, wherein the gel structure contains a polyacrylamide derivative expressed by a chemical formula presented below:

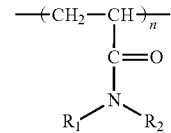

wherein $R_1$ and $R_2$ each denote a chemical structure in which an alkyl group composed of twenty of less hydrogen atoms and carbon atoms or an alkyl group composed of twenty or less carbon atoms contains at least one of a hydroxyl group, a sulfone group, an ether bond, and nitrogen atoms.

10. The tissue mimicking phantom according to claim 8, wherein the oxidic microparticles include at least one of titanium-oxide microparticles, aluminum-oxide microparticles, and silicon-oxide microparticles.

11. A tissue mimicking phantom including a plurality of portions that is different from one another in terms of hardness and an ultrasonic echo property, wherein:
the plurality of portions contains a gel structure having a liquid bound in a polymeric framework, and also contains a solid scatterer, and
wherein the solid scatterer contains at least one kind of resin particles.

12. The tissue mimicking phantome according to claim 11, wherein the gel structure contains a polyacrylamide derivative expressed by a chemical formula presented below:

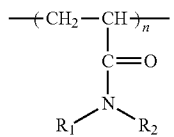

wherein $R_1$ and $R_2$ each denote a chemical structure in which an alkyl group composed of twenty or less hydrogen atoms and carbon atoms or an alkyl group composed of twenty or less carbon atoms contains at least one of a hydroxyl group, a sulfone group, an ether bond, and nitrogen atoms.

13. The tissue mimicking phantom according to claim 11, wherein the resin particles include at least one of polyethylene particles, polyethylene hollow spheres, and polystyrene hollow spheres.

* * * * *